Figure 1:
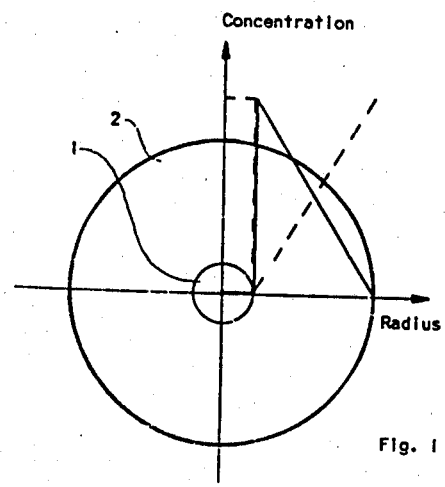
Figure 1:
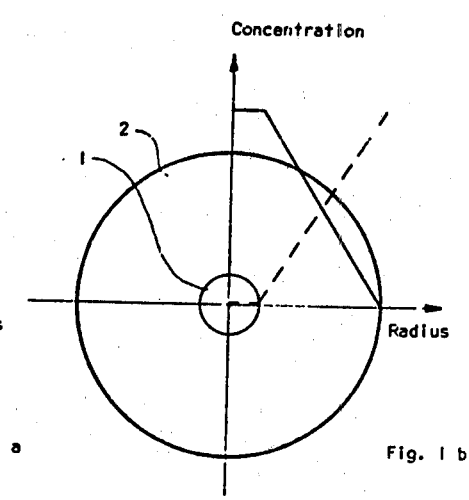
Figure 1:
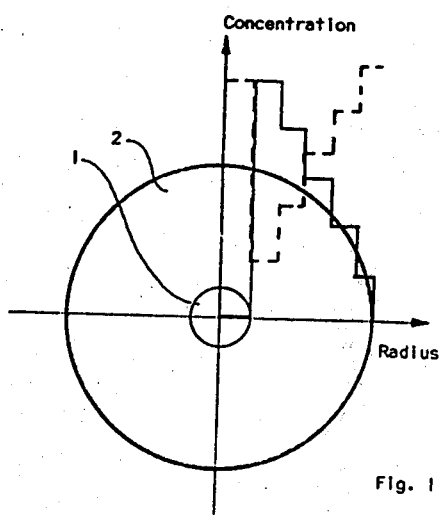
Figure 1:
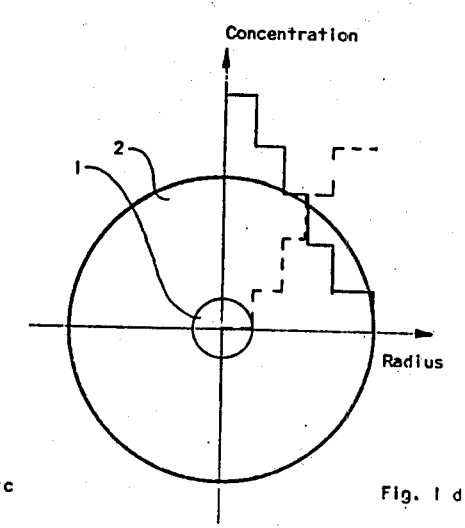

United States Patent [19]

Bogentoft et al.

[11] 4,289,795

[45] Sep. 15, 1981

[54] METHOD FOR PREPARING PREPARATIONS HAVING CONTROLLED RELEASE OF AN ACTIVE COMPONENT

[75] Inventors: Conny B. Bogentoft, Mölndal; Curt H. Appelgren, Frölunda, both of Sweden

[73] Assignee: Aktiebolaget Hassle, Molndal, Sweden

[21] Appl. No.: 13,124

[22] Filed: Feb. 21, 1979

Related U.S. Application Data

[63] Continuation of Ser. No. 742,283, Nov. 16, 1976, abandoned.

[30] Foreign Application Priority Data

Nov. 17, 1975 [SE] Sweden ............................... 7512883

[51] Int. Cl.³ ............................................. A61K 27/12
[52] U.S. Cl. ......................................... 427/3; 424/19; 424/23; 424/21
[58] Field of Search ....................... 424/19, 21, 22, 32, 424/23; 427/3

[56] References Cited

U.S. PATENT DOCUMENTS

2,928,770 3/1960 Bardani ................................. 424/21
3,383,283 5/1968 Brendamour ......................... 424/19

FOREIGN PATENT DOCUMENTS

967610 8/1964 United Kingdom ................. 424/19
1233055 5/1971 United Kingdom ................. 424/19

Primary Examiner—Sam Silverberg
Attorney, Agent, or Firm—Brumbaugh, Graves, Donohue & Raymond

[57] ABSTRACT

A method of preparing a preparation made up by bodies comprising an active component in decreasing concentration towards the surface of the bodies. The method comprises coating a particle with a composition comprising the active component in a continuous coating operation whereby the concentration of the active component is decreased. The active component may be a drug, a pesticide or an agent having some other effect.

12 Claims, 4 Drawing Figures

METHOD FOR PREPARING PREPARATIONS HAVING CONTROLLED RELEASE OF AN ACTIVE COMPONENT

This is a continuation of application Ser. No. 742,283 filed Nov. 16, 1976, now abandoned.

The present invention is related to a method of preparing a preparation comprising one or more active components, which may be given off to a surrounding medium at a controlled rate during a predetermined period of time.

The object of the present invention is to make a preparation which may provide a constant concentration of an active agent, during a predetermined period of time, in a medium, by releasing the agent into the medium, from one or more bodies comprising the agent, at a controlled rate.

The properties of the present invention make it useful especially for preparation of therapeutic preparations intended for oral or local administration. The invention may however be employed to obtain constant release of other active agents, such as pesticides and fertilizers to the surrounding environment.

The most common preparations for drugs are tablets and capsules. This is due to the fact that these preparations are convenient to the patient and that the handling and administration is simple and may be carried out by the patient himself. From ordinary tablets the drug is rapidly released. Such rapid release often leads to an initially highly elevated concentration in the plasma. Drugs which are eliminated relatively rapidly must therefore be administered frequently to avoid reaching concentrations which produce side effects.

In many cases the pharmacological effect of a drug is correlated to a certain concentration thereof in the organism, usually the concentration in blood plasma. Due to this, optimal treatment usually implies that a certain concentration in blood plasma must be maintained, at which concentration the agent exerts its desired effect without giving side effects. Maintenance of an adequate concentration of a drug in the organism requires that the amount of drug supplied corresponds to the amount eliminated from the organism. To fulfil this simple principle one must have access to a preparation which releases the drug at a constant amount per time unit. In certain cases it may be desirable to obtain a release rate which increases during a period of time.

In the commercially available preparations one has attempted in many different ways to sustain the release of the drug. One may, this way, achieve a more even plasma profile, but as the release rate in these known preparations decreases with time one may never obtain a constant level in plasma, which is desirable with many drugs. The preparations, which thus have only one type of release profile are in many instances not sufficiently flexible to provide an optimal way of treatment.

From German Offenlegungsschrift 1 767 765 it is known to prepare multi-layer tablets having different concentration of an active substance in the different layers. The procedure disclosed for preparation of said tablets is repeated pressing to increased diameter in tabletting machine. That procedure is however vary complicated and in reality not useful in rational production of pharmaceuticals. Said procedure further does not make possible preparation of small bodies, such as granules, having decreasing concentration of an active substance. A continuous concentration gradient, further, may not be obtained in bodies prepared according to the procedure thus known, as a discontinuous laying-on takes place and the concentration within each layer is constant.

Problems and drawbacks with the prior art technique have now surprisingly been solved and overcome through the present invention, whereby preparations giving controlled release of an active substance are provided. The invention is related to a process for producing preparations which, on disintegration, release at least one active component at a controlled rate, and characterized in that a particle comprising active and/or inactive material, by a continuous coating operation, is coated with a composition comprising at least said active component and at least one inactive release-controlling substance, is provided with an outer layer having decreasing concentration of said active component in a direction outwards from the particle, to the formation of a body in which the particle forms a core. A negative concentration gradient is thus obtained in the direction outwards in the outer layer of the bodies thus prepared.

According to a preferred embodiment of the invention the continuous coating operation is carried out by spraying of the composition onto the particles, whereby the concentration of the active component in said composition is decreased. Suitably said concentration is decreased by adding to the composition more of an inactive release-controlling substance.

The preparations prepared according to the present invention, comprising one or more active agents in combination with one or more inactive substances, in which preparations the active component is applied with a concentration decreasing towards the surface of the bodies therein, may release the active component to a surrounding medium at a controlled rate. Said rate may be continuously decreasing, continuously increasing or constant during a certain period of time, depending on other factors affecting the release.

The active component may be a drug, a pecticide or an agent having some other effect.

The pharmaceutically active compounds that may be employed in preparations according to the present invention are substantially all those which may be used at oral or local administration in the form of tablets, capsules or granules. Naturally, especially such compounds are employed which are used in long term therapy, such as psychopharmacological agents, blood-fat reducing compounds, compounds active on heart and blood vessels, anti-parkinson-active compounds, digestion-active compounds and compounds in gynaecology and obstretics.

The body prepared according to the invention may have a size from 0.1 to 15 mm, preferably 0.3 to 2 mm. Its shape may be varied but is preferably spherical.

The body is mainly characterized in that the ratio of active substance to other substances increases towards the centre of the body from the surface thereof (viz. FIG. 1 *a–d*, in which 1 denotes a core and 2 denotes the layer applied thereto). The total concentration of active substance in the body may vary within very wide limits, from 0.01 to 99% by weight. The change of concentration in the body may follow a continuous or discontinuous pattern, depending on which active component is used and which profile of release is desired.

The concentration gradient may also be varied to a great extent. The concentration of active substance at a certain point near the centre of the body may be 100 to 0.1% and it may decrease to round 20–0.01% towards the surface of the body, depending on which active component and which type of release-controlling substance are used.

In FIG. 1a is shown schematically a core consisting of inactive substance, on which is applied a composition comprising an active agent with continuous concentration gradient. In each of drawings 1a–d a diagram having its origin at the centre of the body is drawn, wherein concentration along the ordinate has been plotted against the radius along the abscissa. The concentration of active substance is shown by an uninterrupted line and the concentration of inactive substance is shown by a broken line. In FIG. 1b a body is shown in which a core comprising an active substance is coated with a composition comprising an active agent having a continuous concentration gradient. In FIG. 1c is shown a core of inactive material on which a composition is applied comprising an active substance with discontinuous gradient of concentration. In FIG. 1d is shown a core of active substance on which a composition is applied comprising an active substance with discontinuous concentration gradient.

The non-active substances which make part of the preparation have the object of controlling the release rate. One or more such release controlling substances may make part of the same body. Both water-soluble and water-insoluble substances may thereby be employed. The choice of release-controlling agents depends on the type of active component, the amount thereof, and on which rate of release is desired. Preferably lipophilic substances such as waxes, fatty acids and their esters and fatty alcohols are used. Examples of such lipophilic substances are stearic acid, glycerylmonostearate, and cetyl alcohol (cetanol). In the same manner polymers such as polyethylene glycols, polyvinylpyrrolidones, polyvinylacetates, polyacrylates and polymethacrylates or cellulose derivatives, such as ethyl cellulose and hydroxypropyl cellulose may be used. In certain cases water-insoluble dispersable additives, such as talcum and Aerosil ® (silicic acid) may be used.

The body may be built up by one of the usual coating procedures e.g. in a coating pan such as apparatus of the trademark Accela Cota or in fluid bed apparatus. A solution or suspension of the active substance in combination with one or more of the above mentioned auxiliary substances is applied to a core. In this manner a layer round the core is built up. According to the present invention decreasing concentration of the active substance in said layer is achieved through variation of the concentration of active agents in the solution applied to the core.

The particle employed as a core may consist of the active agent alone or mixed with other active or inactive agents. The core may also consist of only one or more inactive substances, e.g. sugar, lactose and starch. Preparation of the core material may advantageously be carried out through a normal granulation procedure. The core may also comprise inert materials such as most plastic materials or other polymers. The size and shape may vary substantially, but preferably spherical granules between 0.1 and 1 mm are used.

The rate of release of the active agent, besides depending on the conditions of releasing employed, depends on the solubility of the active agent in the medium employed, the type and amount of release controlling substances and the geometry and dimensions of the bodies. The desired profile of release is obtained through a suitable adjustment of the concentration gradient and a choice of type and amount of release-controlling substance.

To further direct the release of the active component to a predetermined location, e.g. release in the stomach or to control the release rate, one may apply a suitable polymer film on the body. This may be done in the ordinary manner in e.g. a coating pan or a fluid bed apparatus.

Suitable polymers to be used in this case are of the type used in pharmaceutical industry to coat tablets or granules, e.g. cellulose derivatives, derivatives of acrylic or methacrylic acid, and polyvinylacetate.

Suitable softening agents, such as phthalates, may be added to polymers employed.

EXAMPLE 1

500 g granules ($\phi$0.5–0.75 mm) constituting core material, and consisting of 50% alprenolol×HCl, 25% lactose and 25% starch are sprayed in a fluid-bed apparatus with an alprenolol-cetanol solution for 75 min. 300 g of each substance alprenolol and cetanol are thereby employed. The starting solution consisting of alprenolol×HCl in methylene chloride/methanol solution is first sprayed during 11 minutes. Thereafter the concentration of alprenolol×HCl in the solution is decreased continuously during spraying by adding cetanol in methylene chloride/methanol solution during the last 64 minutes at a rate of 4.7 g/min. The final size is 0.75–1.0 mm.

According to the so called beaker method described by Levy alprenolol is released in water at a temperature of 37° C. at the following rate:
0–5 min = 4.8%/min
5–10 min = 5.2%/min
10–20 min = 4.7%/min The granules obtained may thereafter be coated to control further the release, whereby the above mentioned technique is employed and the following film composition is used:
Etocel N-10 (ethyl cellulose) 50 g + Citroflex A-4 (acetyltributyl citrate) 10 g.

The release according to the beaker method is then
1–6 h = 0.18%/min
6–9 h = 0.14%/min

EXAMPLE 2

500 g metoprolol tartrate granules ($\phi$0.5–0.75 mm), constituting core material, is sprayed during 91 minutes in a fluid-bed apparatus with a solution consisting of metoprolol tartrate 90 g, talcum 40 g, Aerosil ® 10 g, cetanol 10 g and solvents. Into this solution, during the 30–89th minute a solution comprising 300 g cetanol is at a rate of 5.1 g/min. The size of the final coating is 0.75–1.0 mm.

Release in water according to the beaker method is 2.3%/min.

EXAMPLE 3

250 g sugar granules ($\phi$0.5–0.7 mm) are sprayed with a solution comprising 250 g alprenolol×HCl in methylene chloride/methanol. Thereafter the spraying is continued with a second solution comprising 160 g cetanol and 40 g alprenolol×HCl. The granules obtained are coated with a film consisting of Etocel N-10 (ethyl cellulose) 50 g and Citroflex (acetyltributyl citrate) 10 g. The size at finalized coating is 0.75–1.00 mm.

Release according to the beaker method is 6.3%/h.

EXAMPLE 4

500 g of quinidine bisulphate granules, all having a diameter of 0.75–1.0 mm, were sprayed with a solution containing 200 g of cetanol, 50 g of quinidine bisulphate and solvent. The granules are thereafter coated with ethyl cellulose N-10 50 g, Eudragit RS 100, 10 g, and Citroflex A-4 10 g. The size of the finished granules was 1.0–1.2 mm.

Release according to the beaker method 6%/h during 16 h.

EXAMPLE 5

250 g of sugar K 4 were sprayed with 250 g of quinidone bisulphate solution in a fluid-bed apparatus. 500 g of the granules thus obtained were sprayed in a fluid-bed apparatus with a quinidine solution containing 300 g of quinidine bisulphate during 73 minutes. To this solution was continuously added during the course of spraying in the first 56 min. a solution containing 200 g of cetanol at a rate of 3.6 g cetanol/min.

Release according to the beaker method 1.8%/min.

EXAMPLE 6

500 g of alprenolol granules (75%) were sprayed with a solution comprising 300 g of alprenolol during 66 min. To this alprenolol solution was continuously added during the 60 first minutes a solution comprising 300 g of cetanol at a rate of 5 g cetanol/min.

The release rate in percent of the concentration found according to the beaker method after a specified period of time was as shown below.

| Minutes | % |
| --- | --- |
| 10 | 11 |
| 20 | 26 |
| 30 | 38 |
| 40 | 48 |
| 50 | 57 |
| 60 | 66 |
| 90 | 87 |

A solution comprising 500 g of the granules prepared was film coated with a copolymer of methylmetacrylate and ethylacrylate 60 g and Triacetin 5 g. The release rate in % of concentration found according to the beaker method after a specified period of time was as shown below

| hours | % |
| --- | --- |
| 1 | 21 |
| 2 | 44 |
| 3 | 58 |
| 4 | 68 |
| 5 | 77 |
| 6 | 83 |
| 8 | 90 |

Eudragit RS is an acrylic resin (copolymer of acrylic and metacrylic acid esters). Citroflex A-4 is an acetyl tributyl citrate. Triacetin is a glycerol triacetate.

It is considered especially advantageous to employ the present invention in preparation of granules containing quinidine as an active substance. The best way known at present for preparing such granules is shown by Example 5 above. It is further considered advantageous to provide granules thus prepared with a film coating and to fill them into gelatine capsules.

I claim:

1. A process for producing a preparation comprising a plurality of granules each having a core and a unitary layer thereon containing at least one pharmaceutically active material which, on disintegration, release said pharmaceutically active material at a controlled rate, comprising applying to said cores in a continuous coating operation a solution or suspension containing at least one active compound and at least one pharmaceutically inactive release controlling substance over a period of time sufficient to cause said unitary layer of said active ingredient and inactive release controlling substance to form on each core to give granules of size 0.3–2 mm, during said time period the concentration of active ingredient being decreased in the solution or suspension from which the layer is formed by adding additional release controlling substance to the solution or suspension, whereby there results granules each having a layer containing an active ingredient in which layer the concentration of active ingredient decreased radially outwardly from the core to the outer surface of said layer.

2. A process according to claim 1, wherein said continuous coating is carried out by spraying said composition comprising active ingredient and inactive release controlling substance onto said core.

3. A process according to claim 1, wherein the concentration of active ingredient in said solution or suspension decreases continuously with time, whereby the concentration of active ingredient in the layer on said core decreases continuously toward the surface thereof.

4. A process according to claim 1, wherein the concentration of active ingredient in said solution or suspension is decreased during the time of coating in a discontinuous change, whereby a discontinuous gradient of concentration toward the surface of said layer is obtained.

5. A process according to claim 1, wherein the inactive release controlling substance has lipophilic characteristics.

6. A process according to claim 1, wherein said inactive release controlling substance is a water-soluble polymer.

7. A process according to claim 1, wherein the inactive release controlling substance is insoluble and dispersable in water.

8. A process according to claim 1, wherein said biologically active material is a therapeutically active component.

9. A process according to claim 1, wherein the core, before application of the outer layer, has a diameter of at least 0.05 mm.

10. A process for producing a preparation comprising a plurality of granules, each granule having a core and a unitary layer thereon containing at least one pharmaceutically active material which, on disintegration, release said pharmaceutically active material at a controlled rate, comprising applying to said cores in a continuous coating operation a solution or suspension containing at least one pharmaceutically active compound and at least one pharmaceutically inactive release controlling substance selected from the group consisting of waxes, fatty acids, fatty acid esters, fatty alcohols, polyethylene glycols, polyvinylpyrrolidones, polyvinylacetates, polyacrylates, polymethacrylates, cellulose derivatives, talcum and silicic acid, over a period of time sufficient to cause said unitary layer of said active ingredient and inactive release controlling substance to form on each core to give granules of size 0.3–2 mm, during said time period the concentration of active ingredient being decreased in the solution or suspension from which the layer is formed by adding additional release controlling substance to the solution or suspension, whereby there results granules each having a layer containing an active ingredient in which layer the concentration of active ingredient decreases radially outwardly from the core to the outer surface of said layer.

11. A process for producing a preparation comprising a plurality of granules each having a core and a unitary layer thereon containing at least one biologically active material which, on disintegration, release said biologically active material at a controlled rate, comprising applying to said cores in a continuous coating operation a solution or suspension containing at least one active compound and at least one biologically inactive release controlling substance over a period of time sufficient to cause said unitary layer of said active ingredient and inactive release controlling substance to form on each core to give granules of size 0.3–2 mm, during said time period the concentration of active ingredient being decreased in the solution or suspension from which the layer is formed by adding additional release controlling substance to the solution or suspension, whereby there results granules each having a layer containing an active ingredient in which layer the concentration of active ingredient decreases radially outwardly from the core to the outer surface of said layer.

12. A process for producing a preparation comprising a plurality of granules, each granule having a core and a unitary layer thereon containing at least one biologically active material which, on disintegration, release said biologically active material at a controlled rate, comprising applying to said cores in a continuous coating operation a solution or suspension containing at least one active compound and at least one biologically inactive release-controlling substance selected from the group consisting of waxes, fatty acids, fatty acid esters, fatty alcohols, polyethylene glycols, polyvinylpyrrolidones, polyvinylacetates, polyacrylates, polymethacrylates, cellulose derivatives, talcum and silicic acid, over a period of time sufficient to cause said unitary layer of said active ingredient and inactive release controlling substance to form on each core to give granules of size 0.3–2 mm, during said time period the concentration of active ingredient being decreased in the solution or suspension from which the layer is formed by adding additional release controlling substance or suspension, whereby there results granules each having the concentration of active ingredient decreases radially outwardly from the core to the outer surface of said layer.

* * * * *

UNITED STATES PATENT AND TRADEMARK OFFICE
CERTIFICATE OF CORRECTION

PATENT NO. : 4,289,795
DATED : September 15, 1981
INVENTOR(S) : Bogentoft et al.

It is certified that error appears in the above—identified patent and that said Letters Patent is hereby corrected as shown below:

Col. 1, line 63, "vary" should read --very--;
Col. 2, line 40, "pecticide" should read --pesticide--;
Col. 3, line 1, "round" should read --around--;
Col. 4, line 54, after "is" insert --added--;
Col. 4, line 68, "at finalized" should read --of the final--;
Col. 5, line 52, under "hours" insert --1--;
Col. 5, line 56, "68" should read --69--;
Col. 6, lines 49-50, "biologically" should read --pharmaceutically--;
Col. 8, line 26, "decreases" should read --decreasing--.

Signed and Sealed this

Twenty-ninth Day of June 1982

[SEAL]

Attest:

GERALD J. MOSSINGHOFF

Attesting Officer    Commissioner of Patents and Trademarks